United States Patent [19]

Grisoni

[11] Patent Number: 5,010,115
[45] Date of Patent: Apr. 23, 1991

[54] SILICONE FOAMS

[75] Inventor: Bernard F. Grisoni, El Toro, Calif.

[73] Assignee: Dow Corning France S. A., Valbonne, France

[21] Appl. No.: 598,526

[22] Filed: Oct. 16, 1990

[30] Foreign Application Priority Data

Oct. 23, 1989 [FR] France ............... 89 13820

[51] Int. Cl.$^5$ ............................................. C08J 9/02
[52] U.S. Cl. ................................. 521/154; 521/134;
525/477; 528/15; 528/31
[58] Field of Search .............. 521/134, 154; 525/477;
528/15, 31

[56] References Cited

U.S. PATENT DOCUMENTS

| 4,855,328 | 8/1989 | Smith | 521/154 |
| 4,870,115 | 9/1989 | Itoh et al. | 521/154 |
| 4,871,781 | 10/1989 | Weise | 521/154 |
| 4,879,317 | 11/1989 | Smith et al. | 521/154 |
| 4,931,485 | 6/1990 | Inoue et al. | 521/154 |
| 4,954,533 | 9/1990 | Modic | 521/154 |

Primary Examiner—Morton Foelak

Attorney, Agent, or Firm—Howard W. Hermann

[57] ABSTRACT

The invention relates to silicone foams.

It concerns a silicone foam composition consisting of two or more components, the said composition being capable of rapid cure at 20° C. on mixing its components, to give a foamed mass having a density of less than 200 kg/m$^3$, characterised in that it comprises (A) one or more polysiloxanes having at least three alkylhydrogensiloxane units per molecule, (B) one or more polydiorganosiloxanes having at least two siloxane units of the formula

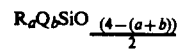

$$R_aQ_bSiO_{\frac{(4-(a+b))}{2}}$$

in which R represents a monovalent hydrocarbon group containing from 1 to 20 carbon atoms, Q represents a hydroxylated alkylene or alkoxylene chain, a has a value of 0, 1 or 2 and the value of b is 1 or 2 and c is a platinum catalyst for promoting the reaction between the components.

Useful for the production of medical dressings.

10 Claims, No Drawings

SILICONE FOAMS

This invention is concerned with improvements in or relating to silicone foams.

Liquid, foam forming, curable compositions are available which flow and foam readily at room or slightly elevated temperature to provide a cured foam product. It has been proposed to employ foamable silicone based room temperature curable compositions for various purposes, including the preparation of medical dressings. Compositions for this purpose are disclosed, for example, in French Patent specifications 2589872 and 2589737. The compositions referred to therein comprise an organosilicon polymer including siloxane units providing a silicon-bonded hydroxyl group, an organosilicon polymer including siloxane units having a silicon-bonded hydrogen atom, a catalyst, for example a tin compound, and finely divided filler comprising silica which has been treated to render it hydrophobic. The compositions cure according to the scheme ≡SiOH+≡SiH→≡Si—O—Si≡+H$_2$. Whilst satisfactory in many ways, the tin catalysed compositions disclosed in French patent specification 2589872 are regarded as less than satisfactory in that it has been suggested that the catalysts and/or derivatives thereof may have some undesirable toxic effects.

Proposals have been made relating to the formulation of silicone rubber foams without using tin compound catalysts. Many of the formulations employ polydiorganosiloxanes having silicon bonded vinyl groups available for reaction with polydiorganosiloxanes having silicon-bonded hydrogen atoms. The addition reaction which occurs is appropriate to yield chain extended or cross linked elastomeric silicone products, but does not generate volatile materials for causing foaming in the composition during cure. A foaming reaction may be induced in such formulations by inclusion of a polydiorganosiloxane having silicon-bonded hydroxyl groups among the ingredients with a view to reaction with the polydiorganosiloxane having silicon-bonded hydrogen atoms as more fully described for example in U.S. Pat. No. 4,026,845, with or without the presence of water, or an aliphatic alcohol as more fully described for example in U.S. Pat. No. 4,613,630, or by inclusion in the composition of a volatile blowing agent as more fully described for example in U.S. Pat. No. 4,550,125.

U.S. Pat. No. 4,492,775 discloses a foam composition which has improved thixotropy and long pot life. Essential ingredients of the composition are polysiloxanes having silicon-bonded hydroxyl groups and polysiloxanes having SiH functionality, a platinum catalyst and inhibitor. The improved properties are said to be achieved through a combination of filler of a certain particle size and less than 10% of a carbinol siloxane or carboxy siloxane or a partially esterified polyfuncitonal alcohol, These additive siloxanes are of viscosity less than 1 PaS and are of the formula

where R' is a monovalent hydrocarbon, R" is R$^3$OH or R$^3$COOH where R$^3$ is a divalent hydrocarbon group.

Applicant's attempts to employ foamable compositions based on polydiorganosiloxanes having silicon-bonded hydrogen atoms and silicon-bonded vinyl groups have not resulted in compositions which cure and foam suitably to form foamed dressings in situ on a patient's body. In particular they do not always cure satisfactorily in contact with moist wound surfaces and may even exhibit an uncured, liquid surface layer, some cure too slowly for convenient use and others do not yield a foam of desirably low density and structure. It is believed that the failure to cure at the surface of the foam is due to interference by water present on the surface with the balance of hydroxylated reactants and SiH groups required for desired platinum catalysed curing and foaming reactions. Desirably compositions intended for in situ provision of medical dressings are curable at room temperatures of the order of 20° C. ±4° C. within 60 seconds ±40 seconds of application to yield a foam of uniform fine pores having a density between 100 Kg/m$^3$ and 300 Kg/m$^3$ and having a major proportion of open cells.

It is one of the various objects of the present invention to provide an improved foamable silicone composition which may be readily mixed and dispensed to form quickly a low density foam and which is suitable for use in providing medical dressings.

The Applicant has now found that an improved platinum catalysed silicone foam composition may comprise as hydroxyl bearing polysiloxane component a polysiloxane having carbon-bonded hydroxyl groups.

The present invention provides in one of its aspects a foamable silicone composition in two or more parts comprising (A) one or more polysiloxanes having not less than three alkylhydrogensiloxane units per molecule, (B) one or more polysiloxanes having hydroxyl groups, and (C) a platinum catalyst for promoting reaction between the components (A) and (B) characterised in that at least a major proportion of the polysiloxanes (B) is a polydiorganosiloxane having at least two siloxane units of the formula

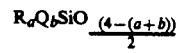

in which R represents a monovalent hydrocarbon group containing 1 to 20 carbon atoms, Q represents a hydroxyl bearing alkylene or oxyalkylene chain, a has the value 0, 1 or 2 and b has the value 1 or 2.

Foamable compositions according to the invention foam and cure according to the scheme ≡SiH+HOQ-Si≡→≡SiOQSi≡+H$_2$. By virtue of the plurality of silicon-bonded hydrogen atoms and hydroxyl groups of the polysiloxanes a network of interconnected polysiloxane chains is produced and the hydrogen evolved as a gas serves to form cells within the developing network. The polysiloxanes and other ingredients and the proportions thereof are selected so that the network is sufficiently developed and cured to produce a resilient foam of desired cellular structure within a short period of time of the order of two minutes or less.

Suitable polysiloxanes having alkylhydrogensiloxane units include polymers having units according to the general formula

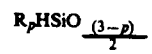

in which each R represents a monovalent hydrocarbon group containing 1 to 20 carbon atoms, for example a lower alkyl or phenyl group e.g. a methyl group, and p is 1 or 2. The alkylhydrogen polysiloxanes may also comprise units $$R_nSiO_{\frac{(4-n)}{2}} \quad (i)$$

in which R is as referred to above and n is 1, 2 or 3.

Reactions of the preferred compositions to generate hydrogen gas and to cure the mass through chain extension and crosslinking within the desired time span are dependant on presence of appropriate proportions of the interactive substituents and the alkylhydrogen polysiloxane is selected accordingly. Preferably this polysiloxane has from 0.5% to 2.5% by weight of silicon-bonded hydrogen atoms We prefer that each R represents a methyl group. Preferably terminal groups of the alkylhydrogen polysiloxane have the formula $R_3SiO_{17\text{s}}$ where each R represents a methyl group. Suitable alkylhydrogen polysiloxanes include those comprising MeHSiO units with or without the presence of $Me_2SiO$ units and having viscosities of the order of from about 1 to about 1000 mm$^2$/s more preferably from about 5 to about 50 mm$^2$/s.

Compositions according to the invention comprise one or more polydiorganosiloxanes (B) having at least two siloxane units of the formula $$R_aQ_bSiO_{\frac{(4-(a+b))}{2}}$$

in which Q represents a hydroxyl bearing alkylene or oxyalkylene chain. The chain may be attached to the silicon atom in any convenient way but is preferably linked to the silicon atom by a carbon atom. Suitable hydroxyl bearing chains include those containing up to 50 chain atoms. Suitable alkylene chains are those having 1 to 15, more preferably 4 to 10 chain carbon atoms Suitable oxyalkylene chains include those of the formula $(C_dH_{2d}O)_eH$ in which d has the value 2, 3 or 4 and e has a value in the range 1 to 15 more preferably 1 to 10, i.e. having from 1 to 15, more preferably 1 to 10 oxyalkylene groups The oxyalkylene groups may be for example oxyethylene, oxypropylene or oxybutylene or mixtures thereof, the most preferred being the oxyethylene group. The alkylene or oxyalkylene chain may have a substituted or unsubstituted chain and may be linear or branched and bears at least one hydroxyl group which may be a primary, secondary or tertiary alcohol group. Examples of suitable alkylene chains are in particular:
—CH$_2$CH$_2$CH$_2$OH, —CH$_2$CHCH$_3$CH$_2$OH- ,—CH$_2$CH$_2$C(CH$_3$)$_2$OH, —CH$_2$CH$_2$CH$_2$CH$_2$OH, —CH$_2$CH$_2$CH(CH$_2$OH)CH$_2$OH, —CH$_2$CH$_2$-C(OH)(CH$_3$)CH$_2$CH$_3$, CH$_2$CH(OH)CH$_2$OH, —CH$_2$CH$_2$C(OH)(CH$_3$)CH$_2$CH(CH$_3$)CH$_3$, —CH$_2$CHCH$_3$CH$_2$OH, —CH$_2$CH$_3$CHCH$_2$OH and CH$_2$CHC$_6$H$_4$OH.

Examples of suitable oxyalkylene chains are in particular: —CH$_2$CH$_2$CH$_2$OCH$_2$CH$_2$CH$_2$OH, —CH$_2$CH$_2$C-H$_2$OCH$_2$CH(OH)CH$_2$OH, —CH$_2$CH$_2$CH$_2$OCH$_2$C(C-H$_2$OH)$_2$CH$_2$CH$_3$, —CH$_2$CH$_2$CH$_2$OCH(CH$_2$OH)CH$_2$OH, —CH$_2$CH$_2$CH$_2$(OCH$_2$CH$_2$CH$_2$)$_3$OH, and —(CH$_2$CH$_2$O)$_{10}$H.

The polydiorganosiloxane (B) also comprises siloxane units (i) as aforesaid. As with the polysiloxane (A), the R groups of the various siloxane units of polydiorganosiloxane (B) represent a monovalent hydrocarbon group containing 1 to 20 carbon atoms, and are preferably methyl groups. The proportion of siloxane units (i) in the polydiorganosiloxane (B) is not critical, and the units of the formula $$R_aQ_bSiO_{\frac{(4-(a+b))}{2}}$$

may be present as chain units or as terminal units of polydiorganosiloxane (B). These substances are preferably liquids and are chosen so that their functionality and chain length is appropriate in relation to the amount of hydrogen evolution and the degree of chain extension and crosslinking required during curing of the composition. Preferably the polydiorganosiloxane has a viscosity in the range 1 mm$^2$/s to 1000 mm$^2$/s more preferably in the range 50 mm$^2$/s to 200 mm$^2$/s.

Platinum catalysts (C) may take any of the known forms ranging from platinum as deposited on carriers such as silica gel or powdered charcoal, to platinic chloride, salts of platinum and chloroplatinic acids. A preferred form of platinum is chloroplatinic acid either as the commonly obtainable hexahydrate or the anhydrous form, on account of its easy dispersibility in organosilicon systems and the absence of any effect on the color of the mixture. Platinum complexes may also be used e.g. those prepared from chloroplatinic acid hexahydrate and divinyl tetramethyldisiloxane. Compositions according to the invention foam and cure very rapidly when the component parts have been mixed together If it is desired to prolong the cure time, for example if it is desired to mix the composition and then transfer it to the site where it is intended to foam and cure, one may include in the composition one of the known platinum catalyst inhibitors such as a cyclic polymethylvinylsiloxane compound or an acetylenic alcohol e.g. methyl butynol.

Compositions according to the invention may also include one or more alcohols. These materials influence the structure of foams formed by use of the composition and have a significant influence on the density of the cured foam. The alcohol is selected with a view to contributing not only generation of hydrogen gas but also with a view to achieving desired softness and resilience of the foam. Suitable alcohols include the primary aliphatic monofunctional alcohols having up to 8 carbon atoms, e.g. ethanol and n-propyl alcohol, and benzyl alcohol. Foams of lowest density are formed by use of the aliphatic alcohols having from 2 to 12 chain carbon atoms. For some purposes, the commonly available alcohols, for example ethanol yield satisfactory results but, particularly when significant proportions of the alcohol are to be used, the hydrophobic alcohols i.e. those of higher molecular weights are preferred.

If desired, other materials having hydroxyl groups reactive with the silicon-bonded hydrogen atoms may be included in minor proportions but it is important to ensure that their inclusion does not lead to unacceptable loss of hydrophobicity of the composition. Such other materials may be for example silanol terminated polydioganosiloxanes according to the general formula $HO((R_2)SiO)_sH$ in which each R represents a methyl group and s has a value from about 10 to about 40. Suitable materials have viscosities of the order of about 50 mm$^2$/s to about 2500 mm$^2$/s. Other substances which may be included as crosslinking agents include compounds having three or more functional e.g. hydroxy groups per molecule.

One may also include in the composition appropriate quantities of substances intended to assist in formation of the polymer network for example silicon based substances, for example polysiloxanes having siloxane units according to the general formula

in which each R represents a monovalent hydrocarbon group having up to 20 carbon atoms, for example a lower alkyl or phenyl group e.g. a methyl radical, m is 1 or 2 and R' represents an aliphatically unsaturated group for example cyclohexenyl or a group R"RCH=CH=CHR"' where R" represents a divalent aliphatic chain linked to the silicon atom and R"' represents a hydrogen atom or an alkyl group for example vinyl, allyl, or hexenyl. These polysiloxanes also comprise units (i) in which R and n are defined as above These substances are reactive with the silicon-bonded hydrogen atoms in presence of the platinum catalyst by a hydrosilylation reaction and thus contribute to the polysiloxane matrix. Preferably, these polysiloxanes have from 0.01% to 1% by weight of aliphatically unsaturated groups and a viscosity of the order of about 10mm$^2$/s to about 25000 mm$^2$/s. More preferably their viscosity lies in the range 100 mm$^2$/s to 2000 mm$^2$/s.

Compositions according to the invention foam and cure rapidly as mentioned above and it is not generally essential to employ foam stabilisers or surfactants in compositions intended for mixing by hand e.g. with a spatula. However, if it is intended to mix and apply the composition under circumstances where the curing reaction is expected to be retarded, it is preferred to include a foam stabilising material. Suitable foam stabilising materials include fluorinated silicones, for example a polyorganosiloxane comprising

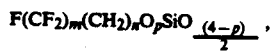

R$_3$SiO$_{1/8}$, SiO$_{4/2}$ units, silicon-bonded hydroxyl groups wherein each R represents a monovalent hydrocarbon group containing from 1 to 20 carbon atoms, n has the value 1 or 2, p has the value 1, 2 or 3. The polysiloxane may also include from 0 to 10 percent, based on the weight of said polyorganosiloxane, of GSiO$_{1/70}$ units wherein G represents the residue obtained by removing the hydrogen atom from a hydroxyl group of a linear organic polymer selected from the group consisting of homopolymers of ethylenically unsaturated alcohols, copolymers of these alcohols with ethylenically unsaturated hydrocarbons, polyethers and polyoxyalkylene glycols, wherein said organic polymer contains an average of at least one terminal hydroxyl group per molecule. These materials may be prepared by treatment of hexamethyldisiloxane coated polysilicates with the alcohol F(CF$_2$)$_8$CH$_2$CH$_2$OH, and are more fully described and claimed in European Patent Specification 179 598.

If desired other additives may be included in a composition according to the invention, for example, fillers, colorants, colored indicators and extenders. However, in general the inclusion of fillers is not preferred.

Compositions according to the invention may be formulated to cure within a short period of time, In order to achieve this, it is important that the units of the formula

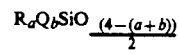

of the polydiorganosiloxane (B) are present in sufficient proportion that the ratio of silicon-bonded hydrogen atoms of the polysiloxane (A) to carbon-bonded hydroxyl groups of the polysiloxane (B) is in the range 1:1 to 20:1 and preferably in the range 2:1 to 10:1. The ratio of silicon-bonded hydrogen atoms to all carbon-bonded hydroxyl groups together with other reactive hydroxyl, unsaturated and other groups present in the composition is preferably in the range 1:1 to 20:1 and is more preferably in the range 2:1 to 9:1. The ratio of silicon-bonded hydrogen atoms to carbon-bonded hydroxyl groups and silicon-bonded hydroxyl groups is suitably in the range 2:1 to 25:1 more preferably 5:1 to 11:1. The ratio of aliphatically unsaturated groups to silicon-bonded hydrogen atoms is preferably in the range 0:1 to 0.5:1 more preferably in the range 0.01:1 to 0.03:1. The ratio of aliphatically unsaturated groups to the total carbon-bonded hydroxyl groups and silicon-bonded hydroxyl groups may be in the range 0:1 to 1:1, more preferably 0.2:1 to 0.5:1.

The Applicant has found that compositions according to the invention in which the ingredients are present in the preferred ratios can be formulated to cure within 20 to 40 seconds of hand mixing of the composition at room temperature (i.e. of the order of 18° C.±2° C.) and humidity (i.e. about 60% to 80% relative humidity) to provide cured foams of a density between about 40kg/m$^3$ and 300 kg/m$^3$ or less. The foams are fine pored foams of uniform cell size They are hydrophobic and generally comprise from about 20% to about 80% closed cells and correspondingly about 80% to about 20% open cells, the more closed cell foams being produced when increased proportions of the foam stabiliser are present. The compositions cure to a tack free condition even at those of their surfaces which lie in contact with moist surfaces.

Compositions according to the invention foam and cure when mixed at room temperature and humidity. Accordingly, the component (A) is stored separated from the component (C) until required for use. In order to a simplify and facilitate mixing the components at the application site, it is preferred to store the compositions in two-part form in which each of the parts is of substantially the same viscosity so that the first and second parts may be mixed together in a ratio of 1:1 by volume or 1:1 by weight as desired. For many purposes it is satisfactory to store the component parts in containers from which they may be subsequently dispensed for hand mixing. However, if desired they may be mixed using a mechanical mixing device or they may be stored in and dispensed from aerosol type dispensers or barrier packs of known kind. For example, the ingredients may be stored as two components, where the polydiorganosiloxane (A) is kept separate from the catalyst (C) in separated compartments of one or more packages from which they may be dispensed under the influence of a propellant gas. If desired the proportions of components packaged in aerosol and barrier packs may be arranged so that when packs of the various parts of the composition are to be dispensed and mixed, the packages may be caused to dispense the necessary proportions of the components simultaneously through a static mixer device whereby the components may be efficiently mixed and applied to the site where the cured foam is desired.

Compositions according to the invention are particularly useful in providing foamed medical dressings by application to a wound site. However, they are also suitable for numerous other applications where their rapid room temperature cure characteristics are beneficial. When used for the production of wound dressings, additives conventionally included in dressings may be included in the composition for example pharmaceuticals, biocides, and growth factors.

In order that the invention may become more clear there now follows a description of five example compositions according to the invention. All parts are by weight unless otherwise specified.

EXAMPLES 1 to 5

The example compositions each comprised two parts A and B, and contained ingredients in the amounts shown in Table I. The ingredients of each example composition were mixed together in a glass beaker. It was found that the compositions each cured in 45 seconds or less to provide a fine pored foam of density as shown in the Table when cast onto moist flesh, the compositions yielded well cured foams with no sticky interface between the foam and the flesh.

TABLE I

| Ingredient | Example Composition | | | | |
|---|---|---|---|---|---|
| | 1 | 2 | 3 | 4 | 5 |
| Polysiloxane having silicon-bonded hydrogen atoms | 6.26 | 3.23 | 6.26 | 6.26 | 6.5 |
| Polydiorganosiloxane having carbon-bonded hydroxyl groups | | | | | |
| I | 3.09 | 3.09 | — | — | 6.6 |
| II | — | — | 3.66 | — | — |
| III | — | — | — | 14.2 | — |
| Octan-1-ol | 0.31 | 0.31 | 0.31 | 0.31 | 3.25 |
| Polydiorganosiloxane having unsaturated groups | | | | | |
| IV | 20 | 20 | 20 | 20 | — |
| V | 3.8 | 3.8 | 3.8 | 3.8 | — |
| Foam stabiliser | 0.35 | 0.35 | 0.35 | 0.35 | 0.24 |
| Catalyst | 0.5 | 0.5 | 0.5 | 0.5 | 0.35 |
| Molar Ratio 1 | 8 | 4 | 8 | 8 | 2 |
| Ratio 2 | 10 | 5 | 10 | 10 | 2 |
| Ratio 3 | 0.02 | 0.05 | 0.02 | 0.02 | 0 |
| Ratio 4 | 0.25 | 0.25 | 0.25 | 0.25 | 0 |
| Curing time (seconds) | 45 | 38 | 40 | 40 | 40 |
| Density (Kg/m$^3$) | 190 | 250 | 280 | 180 | 50 |

In the examples, the ingredients used were as follows.

The polysiloxane having silicon-bonded hydrogen atoms was a trimethylsilyl endblocked polymethylhydrogensiloxane having a viscosity of about 30 mm$^2$/s and 1.5 mol % hydrogen.

Polydiorganosiloxane I having carbon-bonded hydroxyl groups was a trimethylsilyl endblocked polydimethylsiloxane having six dimethylsiloxane units and two siloxane units of the formula $RQSiO_2$ in which R represents a methyl group and Q represents the hydroxyl bearing alkylene chain $CH_2CHCH_3CH_2OH$, a viscosity of about 70 mm$^2$/s and 0.23% carbon-bonded hydroxyl groups.

Polydiorganosiloxane II having carbon-bonded hydroxyl groups was a polydimethylsiloxane having endblocking units $(CH_3)_2QSiO$, in which Q represents $HOCH_2CHCH_3CH_2$ and ten dimethylsiloxane units, a viscosity of 100 mm$^2$/s and 1.9 mole % hydroxyl groups.

Polydiorganosiloxane III having carbon-bonded hydroxyl groups was a trimethylsilyl end blocked polydimethylsiloxane having 4.1 mole % units of the formula $CH_3QSiO_2$, in which Q represents $CH_2CH_2CH_2(OCH_2CH_2CH_2)_3OH$, a viscosity of 170 mm$^2$/s and 0.05 mole % hydroxyl groups.

Polydiorganosiloxane IV having silicon-bonded unsaturated groups was a phenylmethylvinylsilyl endblocked polydimethylsiloxane having a viscosity of about 2100 mm:/s and 0.01 mole % vinyl groups.

Polydiorganosiloxane V having silicon-bonded unsaturated groups was a dimethylvinylsilyl endblocked 1 polydimethylsiloxane having a viscosity of about 450 mm$^2$/s and 0.02 mole % vinyl groups.

The foam stabiliser was prepared by treatment of hexamethyldisiloxane coated polysilicates with the alcohol $F(CF_2)_8CH_2CH_2OH$, as more fully described in European Patent Specification 179 598.

Chloroplatinic acid was used as the catalyst.

The value given in Table I for Molar Ratio is the ratio of silicon-bonded hydrogen atoms of the polysiloxane to all carbon-bonded hydroxyl groups together with other reactive hydroxyl, unsaturated and other groups present in the composition. The value given for Ratio 2 is the ratio of silicon- bonded hydrogen atoms to all silicon-bonded and carbon-bonded hydroxyl groups. The value given for Ratio 3 is the ratio of aliphatically unsaturated groups to silicon-bonded hydrogen atoms and the value given for Ratio 4 is the ratio of aliphatically unsaturated groups to carbon-bonded hydroxyl groups and silicon-bonded hydroxyl groups.

That which is claimed is:

1. A foamable silicone composition in two or more parts comprising (A) one or more polysiloxanes having not less than , three alkylhydrogensiloxane units per molecule, (B) one or more polysiloxanes having hydroxyl groups, and (C) a platinum catalyst for promoting reaction between the components (A) and (B) wherein at least a major proportion of the polysiloxanes (B) is a polydiorganosiloxane having at least two siloxane units of the formula

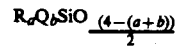

in which R represents a monovalent hydrocarbon group containing 1 to 20 carbon atoms, Q represents a hydroxyl bearing alkylene or oxyalkylene chain, a has the value 0, 1 or 2 and b has the value 1 or 2.

2. A composition according to claim 1 wherein Q represents an alkylene chain having 1 to 15 chain carbon atoms or an oxyalkylene chain of the formula $(C_dH_{2d}O)_eH$ where d has a value 2, 3 or 4 and e has an average value in the range 1 to 10.

3. A composition according to claim 1 wherein the polysiloxane having not less than three alkylhydrogensiloxane units is a polymer having units according to the general formula

with or without the presence of $R_2SiO$ units in which each R represents a methyl group, and p is 1 or 2, and having a viscosity of about 5 to about 50 mm²/s.

4. A composition according to claim 1 also comprising one or more polysiloxanes having not less than two silicon-bonded aliphatically unsaturated groups per molecule and having a viscosity in the range 10 to 25000 mm²/s.

5. A composition according to claim 1 also comprising one or more alcohols.

6. A composition according to claim 1 wherein the proportions of the components (A) and (B) are such that the ratio of silicon-bonded hydrogen atoms to carbon-bonded hydroxyl groups is in the range 1:1 to 20:1.

7. A composition according to claim 1 wherein the proportions of the ingredients are such that the ratio of silicon-bonded hydrogen atoms to carbon-bonded hydroxyl groups and silicon-bonded hydroxyl groups is in the range 2:1 to 25:1.

8. A composition according to claim 1 wherein the proportions of the ingredients are such that the ratio of silicon-bonded hydrogen atoms to carbon-bonded hydroxyl groups and silicon-bonded hydroxyl groups together with other reactive groups present in the composition is in the range 1:1 to 20:1.

9. A composition according to claim 4 wherein the proportions of the ingredients are such that the ratio of silicon-bonded hydrogen atoms to aliphatically unsaturated groups is in the range 1:0 to 1:05.

10. A composition according to claim 1 wherein the ingredients are packaged in two parts with the polysiloxane (A) separate from the catalyst (C) in separated compartments of one or more packages from which they may be dispensed under the influence of propellant gas.

* * * * *